United States Patent
Noone et al.

[19]

[11] Patent Number: 5,916,178
[45] Date of Patent: Jun. 29, 1999

[54] STEERABLE HIGH SUPPORT GUIDEWIRE WITH THIN WALL NITINOL TUBE

[75] Inventors: Michael S. Noone, Londonderry, N.H.; Mark A. Johanson, Littleton, Mass.

[73] Assignee: Medtronic, Inc., Minneapolis, Minn.

[21] Appl. No.: 08/851,392

[22] Filed: May 5, 1997

Related U.S. Application Data

[63] Continuation of application No. 08/414,669, Mar. 30, 1995, abandoned.

[51] Int. Cl.[6] ........................................................ A61B 5/00
[52] U.S. Cl. ............................. 600/585; 604/95; 604/280
[58] Field of Search ................................... 600/585, 433, 600/434; 604/95, 96, 280, 281, 282

[56] References Cited

U.S. PATENT DOCUMENTS

| | | | |
|---|---|---|---|
| 3,789,841 | 2/1974 | Antoshkiw | 128/2.05 |
| 4,841,976 | 6/1989 | Packard et al. | 600/585 |
| 4,854,330 | 8/1989 | Evans, III et al. | 600/585 |
| 4,884,579 | 12/1989 | Engelson | 128/772 |
| 4,911,148 | 3/1990 | Sosnowski et al. | 600/146 |
| 4,925,445 | 5/1990 | Sakamoto et al. | 604/95 |
| 5,067,489 | 11/1991 | Lind | 128/772 |
| 5,069,226 | 12/1991 | Yamauchi et al. | 128/772 |
| 5,230,348 | 7/1993 | Ishibe et al. | 128/772 |
| 5,243,996 | 9/1993 | Hall | 128/772 |
| 5,433,200 | 7/1995 | Fleischnacker, Jr. | 128/657 |
| 5,437,288 | 8/1995 | Schuartz et al. | 600/585 |
| 5,479,938 | 1/1996 | Weier | 128/772 |
| 5,505,699 | 4/1996 | Forman et al. | 604/96 |
| 5,606,981 | 3/1997 | Tartacower et al. | 600/585 |

OTHER PUBLICATIONS

Boyer, Rodney; Welsch, Gerhard; and Collings, E.W.; *Materials Properties Handbook: Titanium Alloys*; Jun. 1994; pp. 1035–1036.

*55–Nitinol–The Alloy with a Memory: Its Physical Metallurgy, Properties, And Applications*, by Jackson et al., 1972, Prepared under contract for NASA. Foreword, pp. 1–2, p. 1037.

*Primary Examiner*—Robert L. Nasser
*Assistant Examiner*—Pamela L. Wingood
*Attorney, Agent, or Firm*—David S. Brin; Dianne Plunkett Latham; Harold R. Patton

[57] ABSTRACT

A guidewire for use in a catheter comprising a unitary core wire, a distal tip and an elongate tube. The core wire has a body segment and a transition segment, the body segment being of substantially uniform outer diameter with a distal end serially disposed proximal to the transition segment proximal end, the transition segment being more flexible than the body segment, and progressively reduced in cross-section from the body segment. The smoothly rounded distal tip is affixed to the distal end of the transition segment. The elongate tube defines a tube lumen, the core wire transition segment extends longitudinally through the tube, the tube having a uniform outer diameter equal to the outer diameter of the body segment, the proximal end of the tube being affixed to the proximal end of the transition segment, the distal end of the tube being affixed to the distal tip. The tube may be formed of a super-elastic metallic member or formed from a synthetic resin. The tube wall thickness is preferably between 0.002 inches and 0.005 inches.

45 Claims, 2 Drawing Sheets

STEERABLE HIGH SUPPORT GUIDEWIRE WITH THIN WALL NITINOL TUBE

This application is a continuation of application Ser. No. 08/414,669 filed on Mar. 30, 1995 now abandoned.

FIELD OF THE INVENTION

The present invention relates to guidewires, and more particularly, to high support guidewires with a flexible tube at the distal end. Such a guidewire can be used in PTCA procedures such as balloon angioplasty, atherectomy, stent implantation procedures, or radiology procedures.

BACKGROUND OF THE INVENTION

One of the therapeutic procedures applicable to the present invention is known as percutaneous transluminal coronary angioplasty (PTCA). This procedure can be used, for example, to reduce arterial build-up of cholesterol fats or atherosclerotic plaque. Typically a guidewire is steered through vascular system to the site of therapy. A guiding catheter, for example, can then be advanced over the guidewire and a balloon catheter advanced within the guiding catheter over the guidewire. The balloon at the distal end of the catheter is inflated causing the site of the stenosis to widen. The original catheter can then be withdrawn and a catheter of a different size or another device such as an atherectomy device can be inserted.

The major considerations in guidewire design include steerability, flexibility, medial stiffness or support, bending in transition areas, tip formability and radiopacity. In a typical guidewire construction a tapered stainless steel core wire has a platinum spring coil wound around the tapered distal end of the core wire. The tapered area of the core wire is called the transition segment. The longer the tapered transition segment, the more flexible the guidewire. A blunt tip is typically welded to the distal end of the guidewire to reduce trauma to the blood vessel.

Support refers to a guidewire's ability to provide a strong "platform" or track for the catheter to move over as it is crossing the lesion. Support becomes crucial when the lesion is tight. Catheters are soft and rely heavily on the support provided by the guidewire. The spring coil is typically used to provide device support and maintain a consistent guidewire outer diameter. If the outer diameter of the guidewire is reduced, it will exert more force per unit area and may result in cutting through the blood vessel rather than tracking through the bends in the vessels. Increasing core wire diameter also assists in providing enhanced support. The spring coil wire is wound into a coil and placed over the core wire. The spring coil proximal end is difficult to attach to the core wire. A typical spring coil is approximately 0.002 inches in diameter thereby providing a very small area with which to attach to the core wire. Spring coil guidewire construction has been known in the art for many years. An early example of such guidewire construction includes U.S. Pat. No. 3,789,841 for a "Disposable Guide Wire" to Antoshkiw.

Transition refers to areas of changing diameter along the guidewire. A smooth transition gives the guidewire the ability to follow itself smoothly around vascular bends. If a stiffer portion of the guidewire behind the flexible tip does not follow the tip around vascular bends, the tip position may be lost. A guidewire with poor or rough transition will show elbows or bends in the vascular curves. Without smooth transitions a guidewire will not corner smoothly. Smooth transitions also facilitate the tracking of the balloon catheter over the wire when crossing the lesion.

U.S. Pat. No. 4,884,579 to Engelson for "Catheter Guidewire" discloses a guidewire with proximal, intermediate and distal sections. The intermediate section has greater lubricity than the adjacent proximal and distal sections. The greater frictional coefficient in the distal end segment acts to anchor the end of the wire in a branch vessel when the guide wire has been advanced across the sharp-bend vessel junction. In FIG. 6, the distal segment of the core wire is incased in a polymer tube having a series of annular grooves to provide increased tube flexibility as well as greater frictional coefficient.

Elastomers and shape memory materials have been used in the catheter industry to promote elasticity and to promote tips that will return to a preformed curve after flexing. Super-elastic guidewires are known in the art, as for example, U.S. Pat. No. 4,925,445, to Sakamoto et al. for "Guide Wire for Catheter" which discloses a guidewire with at least portions of the inner core formed of the super-elastic metallic member. U.S. Pat. No. 5,067,489 to Lind for "Flexible Guide with Safety Tip" discloses an elongated, helically wound coil and an elongated flexible metal core of shape memory alloy. U.S. Pat. No. 5,069,226 to Yamauchi et al. for "Catheter Guidewire with Pseudo Elastic Shape Memory Alloy" discloses a catheter guide wire comprising a solid core wire of Ti-Ni shape memory alloy and an outer jacket covering the core wire. The jacket is made of any one of synthetic resins such as polyethylene, polyvinyl chloride, polyester, polypropylene, polyamide, polyurethane, polystyrene, fluoride resin, silicone rubber, and other elastomers. U.S. Pat. No. 5,243,996 to Hall for "Small-Diameter Superelastic Wire Guide" discloses a mandrel of metallic superelastic material, such as nitinol having a smoothly rounded tip attached to the distal tip of the mandrel and a coil attached at the distal region of the mandrel, the coil coaxially surrounding a portion of the distal region.

SUMMARY OF THE INVENTION

A drawback of spring coils as currently used in guidewires is that their indented surface may not pass through tight lesions effectively and may catch on devices being passed over them such as devices with cutting mechanisms. Another disadvantage is that they may provide too much flexibility for some devices to properly track over. Additionally, the spring coil is difficult to manufacture because it requires the wire to be helically wound with a uniform outer diameter, then placed over the core wire and welded thereto. The spring coil is also prone to separation where it attaches. An object of the invention is to eliminate the need of a guidewire spring coil while maintaining a uniform shaft outer diameter and providing sufficient support for more difficult PTCA procedures such as total occlusions, atherectomy, Rotoblator ® (a registered trademark of Heart Technology, Inc.) and stent delivery. Another object of the invention is to provide steerability for wire placement. Yet another object of the invention is to avoid attachment weakness at the location where the spring coil would have attached to the core wire.

The above objects and advantages of the present invention, as well as others, are accomplished by providing a guidewire for use in a catheter comprising a unitary core wire, a distal tip and an elongate tube. The core wire has a body segment and a transition segment, the body segment being of substantially uniform outer diameter with a distal end serially disposed proximal to the transition segment proximal end, the transition segment being more flexible than the body segment, and progressively reduced in cross-section from the body segment. The smoothly rounded distal tip is affixed to the distal end of the transition segment. The elongate tube defines a tube lumen, the core wire transition segment extends longitudinally through the tube, the tube having a uniform outer diameter equal to the outer diameter of the body segment, the proximal end of the tube being affixed to the proximal end of the transition segment, the distal end of the tube being affixed to the distal tip. The tube may be formed of a super-elastic metallic member or formed from a synthetic resin. The tube wall thickness is preferably between 0.002 inches and 0.005 inches.

DETAILED DESCRIPTION OF THE PREFERRED EMBODIMENTS

Figure 1:
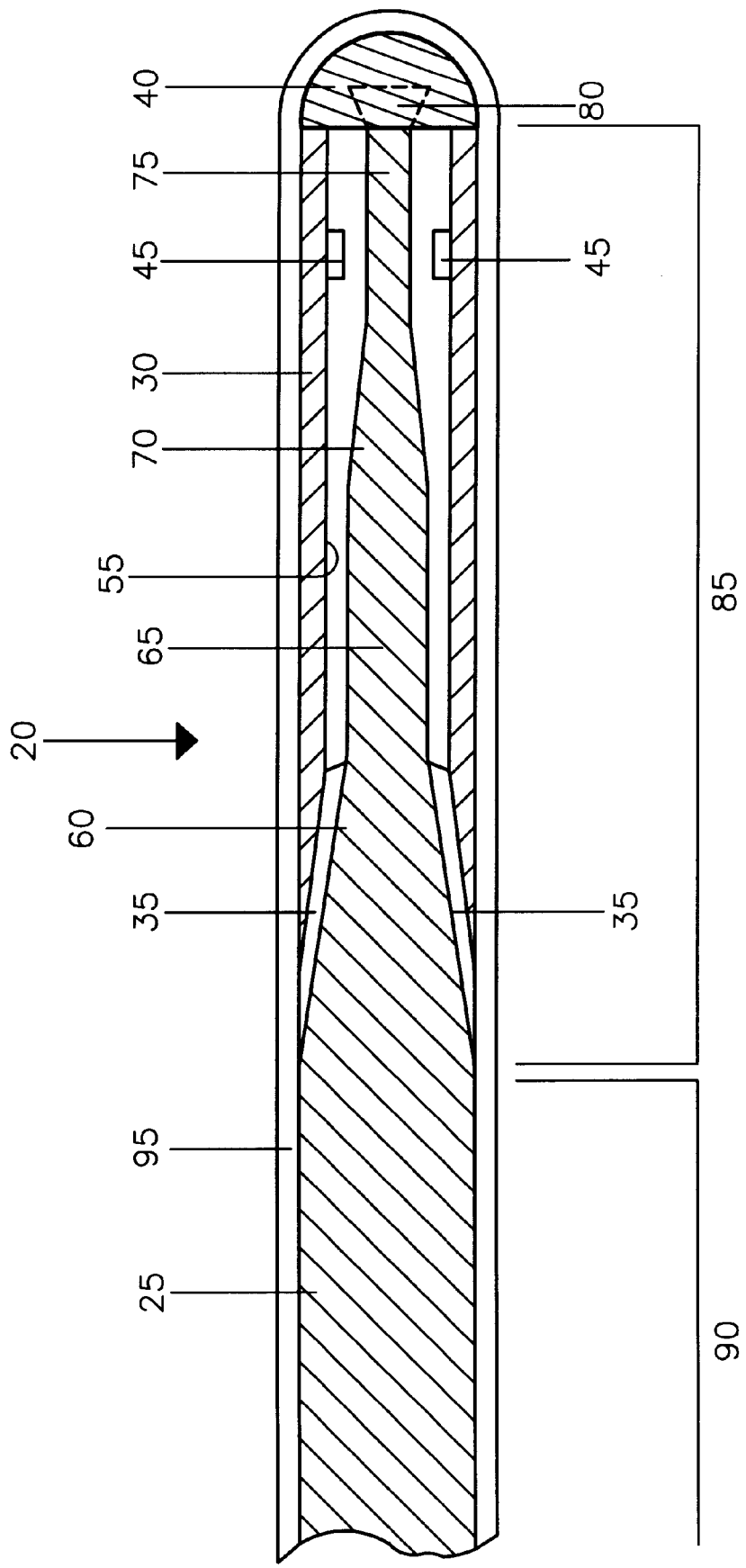
FIG. 1 is an enlarged sectional view of a catheter guidewire according to the invention.
Figure 2:
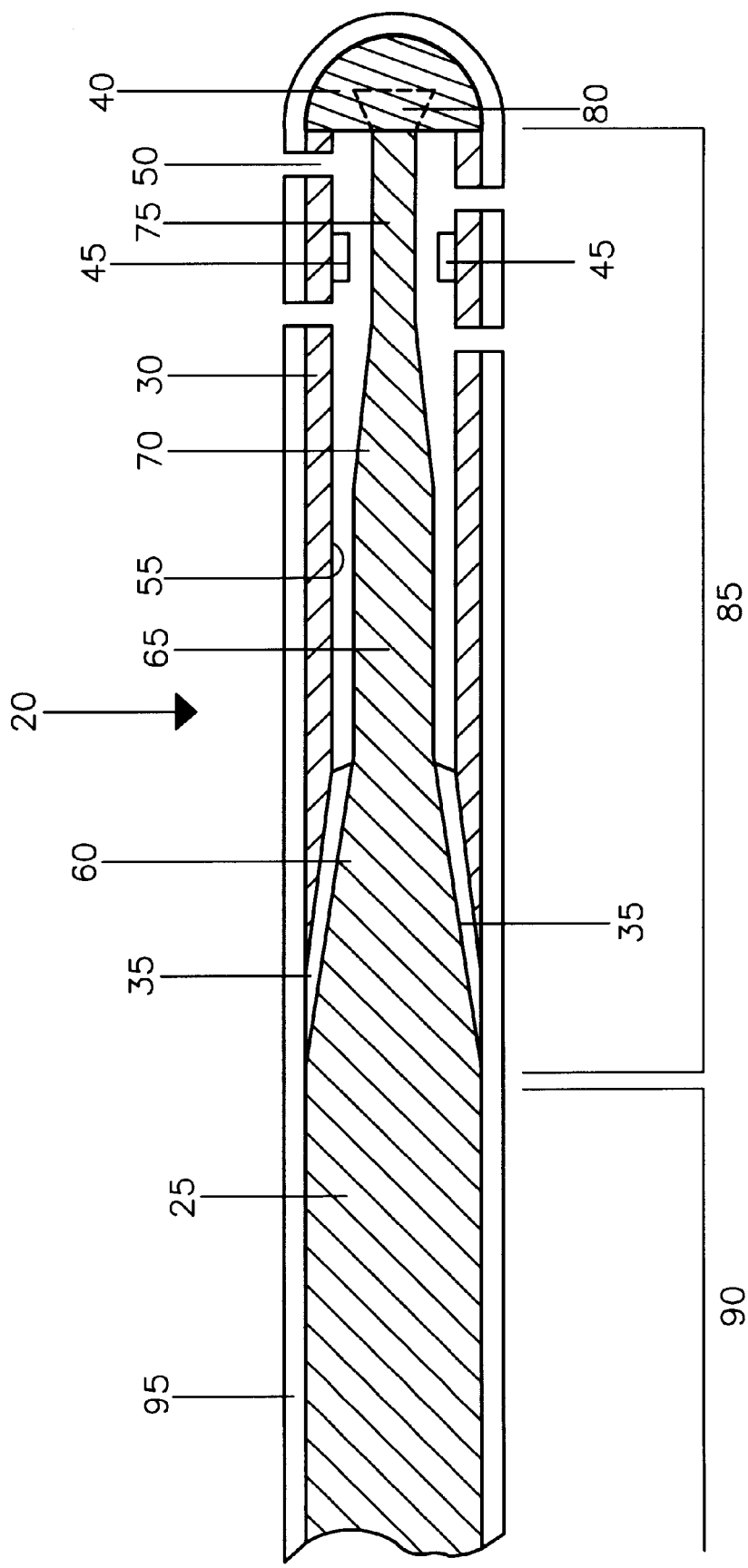
FIG. 2 is an enlarged sectional view of a catheter guidewire according to the invention showing orifices in the tube.

Prior art guidewires are currently constructed with a spring coil over the tapered distal end of the core wire to increase flexibility while maintaining a constant shaft outer diameter. A radiused blunt tip is soldered to the distal end of the core wire and spring coil. Applicant's guidewire 20 is a standard length of 175–310 cm long. Instead of a spring coil, however, applicant's guidewire 20 is constructed using a tube 30 which can be made of an elastomer or an alloy which is highly flexible without permanent deformation such as a shape memory alloy. The tube 30 can be approximately 10 cm to 40 cm long, preferably 0 cm which is the average length from the coronary vessel to the aortic arch. The tube 30 can preferably be made of a shape memory alloy such as nitinol manufactured by Raychem or Forukawa. A preferred embodiment uses NiTi 49–51 atom % Ni.

Shape memory alloys allow one to deform the alloy at a lower temperature with fairly low force and then with merely the application of heat, the material will exert a very strong force as it attempts to regain its previous shape. A useful shape memory alloy property includes an exceptional superelastic springiness if one deforms it at a temperature slightly above the transformation temperature. Shape memory alloys exhibit a very soft, energy absorbing behavior if used just below that temperature.

Examples of shape memory alloys which have a superelastic effect include AgCd 44–49 atom % Cd; AuCd 46.5–50 atom % Cd; CuAlNi 14–14.5 weight % Al, 3–4.5 weight % Ni; CuZn 38.5–41.5 weight % Zn; CuZn X few Weight % X, (X=Si, Sn, Al); InTi 18–23 atom % Ti; NiAl 36–38 atom % Al; NiTi 49–58 atom % Ni; FePt 25 atom % Pt; MnCu 5–35 atom % Cu; FeMnSi 32 weight % Mn, 6 weight % Si.

The use of superelastic NiTi wire has significant advantages over more conventional materials as well as other shape memory alloys. NiTi has a much lower effective modulus than stainless steel. Of the shape memory alloys, the Ni Ti family is the most commercially attractive system. The NiTi alloy has constituents which are not prohibitively expensive, can be fabricated with existing metalworking techniques and have greater shape memory strain (up to 8%) than other alloys. As seen from the shape memory alloy list supra, many contain expensive or exotic elements which are less commercially attractive than NiTi.

Tube 30 can also be made of a synthetic resin elastomer such as any one of polyethylene, polyvinyl chloride, polyester, polypropylene, polyamide, polyurethane, polystyrene, and other elastomers. A fluoropolymer can also be used such as TEFLON® from E.I. Du Pont de Nemours & Company, Wilmington, Del. TEFLON® is a form of polytetrafluoroethylene (PTFE). Elastomers are lower cost then shape memory alloys. Shape memory alloys, however, provide more rigidity for better support than most of the elastomers.

The tube 30 is supported by a distally tapering core wire 25. The core wire 25 can be constructed of stainless steel. Variable stiffness in the core wire 25 can be achieved by step grinding tapers of differing diameters. The first core wire taper 60 from the proximal end of the core wire 25 would be a diameter reduction equal to the thickness of the tube and for a length of 1–5 mm toward the distal end of the tube. The proximal end of tube 30 has a complimentary taper which mates with the taper of the first core wire taper 60. The tube 30 wall thickness varies depending of the size guidewire 20 used. The bigger the guidewire 20, the thicker the tube 30 must be to provide support. For example, a tube 30 wall thickness of 0.002 inches could be used for 0.010 inch diameter guidewires. A tube 30 wall thickness of 0.005 inches could be used for 0.040 inch diameter guidewires. The preferred tube 30 wall thickness is 0.0025 inches. A constant shaft outer diameter is maintained throughout tube 30 by step grinding the distal end of the tube to coincide with the first core wire taper. The remaining core wire is step ground at appropriate intervals suitable for standard guidewires such as 0.010 inch to 0.040 inch diameters. For example, assume a standard 0.014 inch guidewire with a 30 cm tube 30. The first straight segment 65 could have a length of 10–30 cm and would have a diameter of 0.004–0.007 inches. The second taper 70 could have a length of 2–20 mm. The second straight segment 75 could have a length of 2–10 cm and would have a diameter of 0.002–0.005 inches. There can be an optional 50% increased diameter final grind attachment taper 80 at the most distal end of the core wire 25 to allow greater surface area for attaching the distal end of tube 30.

An example of a preferred embodiment would contain the following dimensions. The proximal end of the guidewire body would have a substantially uniform diameter of 0.014 inches. The guidewire core wire body segment 90 and transition segment 85 are made from a unitary piece of material. The first core wire taper 60 would have a length of 1–5 mm tapering down from a diameter of 0.014 inches to a diameter of 0.006 inches. The first straight segment 65 would have a length of 24 cm and a substantially uniform diameter of 0.006 inches. The second core wire taper 70 would have a length of 4 mm and taper down from a diameter of 0.006 inches to a diameter of 0.004 inches. The second straight segment 75 would have a length of 8 cm and a substantially uniform diameter of 0.004 inches. The preferred tube 30 wall thickness would be about 0.0025 inches. This embodiment's dimensions are preferred because they offer the best combination of flexibility and handling properties for the vascular anatomy. The flexible distal section allows the guidewire to bend through tortuous vessels. The first straight segment 65 has a greater diameter than the second straight segment 75. The tapered segments in conjunction with the tube 30 better transmit torque and also provide a firm platform with high support for devices which are tracked over the guidewire.

The proximal end of the tube 30 is attached to the core wire 25 with an adhesive 35 at the first taper 60 along the interface of the tube 30 proximal taper but not within the tube lumen 55. Adhesives such as cyanoacrylates or epoxy may be used for joining the tube 30 to the core wire 25. Those skilled in the art would recognize that any biocompatible adhesive would be satisfactory. The present invention avoids the spring coil proximal end attachment problems of the prior art. A typical spring coil is approximately 0.002 inches in diameter thereby providing a very small area with which to attach to the core wire. The tube 30 of the present invention provides a 360 degree area of attachment to the core wire 25. The larger surface area provides for a more reliable attachment.

A tip 40 is brazed or welded to the distal end of the core wire 25. The tip 40 can be made of radiopaque materials such as epoxy loaded with tantalum so that the physician can visualize the distal portion under fluoroscopy. A second radiopaque marker band 45 can be placed in the distal inner lumen of the tube 30 approximately 1–2 cm from the radiopaque tip 40. The marker band 45 can be attached by heat bonding or with an adhesive such as epoxy. Having two radiopaque areas 40 and 45 gives the physician a sense of scale.

After attaching the tube 30 to the core wire 25, the guidewire 20 is coated with a lubricous coating 95 to enhance the movement of devices over it. The guidewire can be coated with a silicone oil or a hydrophilic coating. The advantage of Silicone is that it is inexpensive and easy to apply. The advantage of a hydrophilic coating is that it absorbs moisture and becomes slippery when inserted into the blood stream.

The tube 30 may be cut, indented, grooved or punctured with holes in order to increase its flexibility. Such orifices 50 could occur along the distal portion of the tube including from the distal 5 cm to the entire length of the tube 30. The distal 2–3 cm usually requires the greatest flexibility and should have the greatest density of orifices 50. An additional 2 cm would provide a transition to the full rigidity of the tube by having a lower density of orifices 50. Flexibility is achieved through a combination of orifice 50 size and density. Many small orifices 50 would be better than a few large orifices 50. A few large orifices 50 could act as a stress point or a propagation point for a fracture.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
|-----|-----------|
| 20  | Guidewire |
| 25  | Core Wire |
| 30  | Flexible Tube |
| 35  | Adhesive |
| 40  | Tip |
| 45  | Radiopaque Marker Band |
| 50  | Orifice |
| 55  | Tube Lumen |
| 60  | First taper |
| 65  | First Straight Segment |
| 70  | Second Taper |
| 75  | Second Straight Segment |
| 80  | Attachment Taper |
| 85  | Transition Segment |
| 90  | Core Wire Body Segment |
| 95  | Lubricous Coating |

What is claimed is:

1. A guidewire for use in a catheter, comprising:

an elongate unitary core wire having a body segment and a transition segment, the body segment being of substantially uniform outer diameter, the body segment having a proximal end and a distal end, the transition segment having an outer diameter, a proximal end and a distal end, the body segment distal end being serially disposed proximal to the transition segment proximal end, the transition segment being more flexible than the body segment, the transition segment being progressively reduced in cross-section from the body segment;

a smoothly rounded distal tip affixed to the distal end of the transition segment; and an elongate tube having an inner diameter, the elongate tube defining a hollow tube lumen, the transition segment extending longitudinally through the tube lumen, the outer diameter of the transition segment being spaced apart from the inner diameter of the elongate tube to define a hollow area having no structure therebetween over at least a major portion of the transition segment for increased flexibility, the tube having a proximal end and a distal end, the tube having a uniform outer diameter equal to the outer diameter of the core wire body segment, the proximal end of the tube being affixed to the proximal end of the transition segment, the distal end of the tube being affixed to the distal tip, the tube being of a unitary, non-coiled construction.

2. The guidewire of claim 1 wherein the transition segment further comprises at least one tapered segment and at least one straight segment, the tapered and straight segments being serially disposed and alternating with each other beginning with a first tapered segment, the first tapered segment having a distal end and a proximal end, the first tapered segment tapering down in outer diameter from the outer diameter of the distal end of the body segment to the outer diameter of the proximal end of the first straight segment.

3. The guidewire of claim 2 wherein the transition segment further comprises a second tapered segment and a second straight segment, the second tapered segment having a proximal end and a distal end, the proximal end being serially disposed distal to the distal end of the first straight segment, the second tapered segment proximal end having an outer diameter equal to the outer diameter of the distal end of the first straight segment, the second straight segment having a proximal end and a distal end, the second straight segment having a substantially uniform outer diameter equal to the outer diameter of the distal end of the second tapered segment.

4. The guidewire of claim 3 wherein the transition segment further comprises an attachment segment having a proximal end and a distal end, the proximal end of the attachment segment being serially disposed distal to the distal end of the second straight segment, the attachment segment proximal end outer diameter being substantially equal to the outer diameter of the distal end of the second straight segment.

5. The guidewire of claim 3 wherein the transition segment further comprises a first tapered segment having a length of about 1–5 mm.

6. The guidewire of claim 3 wherein the transition segment further comprises a first straight segment having a length of about 10–30 cm.

7. The guidewire of claim 3 wherein the transition segment further comprises a first straight segment having an outer diameter of about 0.004–0.007 inches.

8. The guidewire of claim 3 wherein the transition segment further comprises a second tapered segment having a length of about 2–20 mm.

9. The guidewire of claim 3 wherein the transition segment further comprises a second straight segment having a length of about 2–10 cm.

10. The guidewire of claim 3 wherein the transition segment further comprises a second straight segment having an outer diameter of about 0.002–0.005 inches.

11. The guidewire of claim 3 wherein the attachment segment outer diameter is larger at the distal end than at the proximal end.

12. The guidewire of claim 1 wherein tube is formed of an elastomer selected from a group of synthetic resins consisting of polyethylene, polyvinyl chloride, polyester, polypropylene, polyamide, polyurethane, polystyrene and polytetrafluoroethylene.

13. The guidewire of claim 1 wherein the tube is formed of a super-elastic metallic material.

14. The guidewire of claim 1 wherein the tube is formed of a super-elastic metallic member including an alloy selected from the groups consisting of NiTi alloy consisting essentially of 49–58 atom % Ni and the balance substantially Ti, CuZn alloy consisting essentially of 38.5–41.5 weight % Zn and the balance substantially Cu, CuZnX, consisting essentially of few weight % X, (X=Si, Sn, Al), NiAl alloy consisting essentially of 36–38 atom % Al and the balance substantially Ni, CuAlNi 14–14.5 weight % Al, 3–4.5 weight % Ni, MnCu 5–35 atom % Cu, FeMnSi 32 weight % Mn, 6 weight % Si.

15. The guidewire of claim 1 wherein the tube has a plurality of orifices along the tube to cause progressively increasing flexibility towards the distal end of the tube.

16. The guidewire of claim 1 wherein the tube has the same length as the transition segment.

17. The guidewire of claim 1 wherein the tube has a length of about 10–40 cm.

18. The guidewire of claim 1 wherein the proximal end of the tube is adhesively bonded to the proximal end of the transition segment.

19. The guidewire of claim 1 wherein the transition segment has at least one radiopaque marker.

20. The guidewire of claim 1 having an outer surface with a lubricous coating applied thereto.

21. The guidewire of claim 1 wherein the tube of has a wall thickness of between about 0.002 and 0.005 inches.

22. The guidewire of claim 1 wherein the transition segment forms with the elongate tube a tip segment, the tip segment having a curved shape, the tip segment being substantially elastic to flexing of the curved shape, so that, after a flexing of the curved shape, the tip segment returns to the curved shape.

23. A guidewire for use in a catheter, comprising:

an elongate unitary core wire having a body segment and a transition segment, the body segment being of substantially uniform outer diameter, the body segment having a proximal end and a distal end, the transition segment having an outer diameter, a proximal end and a distal end, the body segment distal end being serially disposed proximal to the transition segment proximal end, the transition segment being more flexible than the body segment, the transition segment being progressively reduced in cross-section from the body segment;

a smoothly rounded distal tip affixed to the distal end of the transition segment; and an elongate tube having an inner diameter, the elongate tube defining a hollow tube lumen, the transition segment extending longitudinally through the tube lumen, the outer diameter of the transition segment being spaced apart from the inner diameter of the elongate tube to define a hollow area having no structure therebetween over at least a major portion of the transition segment for increased flexibility, the tube having a proximal end and a distal end, the tube having a uniform outer diameter equal to the outer diameter of the core wire body segment, the proximal end of the tube being affixed to the proximal end of the transition segment, the distal end of the tube being affixed to the distal tip, the tube being of a unitary, non-coiled construction;

the transition segment forming with the elongate tube a tip segment, the tip segment having a curved shape, the tip segment being substantially elastic for flexing of the curved shape, so that, after a flexing of the curved shape, the tip segment returns to the curved shape.

24. The guidewire according to claim 23 wherein the transition segment further comprises at least one tapered segment and at least one straight segment, the tapered and straight segments being serially disposed and alternating with each other beginning with a first tapered segment, the first tapered segment having a distal end and a proximal end, the first tapered segment tapering down in outer diameter from the outer diameter of the distal end of the body segment to the outer diameter of the proximal end of the first straight segment.

25. The guidewire of claim 24 wherein the transition segment further comprises a second tapered segment and a second straight segment, the second tapered segment having a proximal end and a distal end, the proximal end being serially disposed distal to the distal end of the first straight segment, the second tapered segment proximal end having an outer diameter equal to the outer diameter of the distal end of the first straight segment, the second straight segment having a proximal end and a distal end, the second straight segment having a substantially uniform outer diameter equal to the outer diameter of the distal end of the second tapered segment.

26. The guidewire of claim 25 wherein the transition segment further comprises an attachment segment having a proximal end and a distal end, the proximal end of the attachment segment being serially disposed distal to the distal end of the second straight segment, the attachment segment proximal end outer diameter being substantially equal to the outer diameter of the distal end of the second straight segment.

27. The guidewire of claim 25 wherein the transition segment further comprises a first tapered segment having a length of about 1–5 mm.

28. The guidewire of claim 25 wherein the transition segment further comprises a first straight segment having a length of about 10–30 cm.

29. The guidewire of claim 25 wherein the transition segment further comprises a first straight segment having an outer diameter of about 0.004–0.007 inches.

30. The guidewire of claim 25 wherein the transition segment further comprises a second tapered segment having a length of about 2–20 mm.

31. The guidewire of claim 25 wherein the transition segment further comprises a second straight segment having a length of about 2–10 cm.

32. The guidewire of claim 25 wherein the transition segment further comprises a second straight segment having an outer diameter of about 0.002–0.005 inches.

33. The guidewire of claim 25 wherein the attachment segment outer diameter is larger at the distal end than at the proximal end.

34. The guidewire of claim 23 wherein tube is formed of an elastomer selected from a group of synthetic resins consisting of polyethylene, polyvinyl chloride, polyester, polypropylene, polyamide, polyurethane, polystyrene and polytetrafluoroethylene.

35. The guidewire of claim 23 wherein the tube is formed of a super-elastic metallic material.

36. The guidewire of claim 23 wherein the tube is formed of a super-elastic metallic member including an alloy selected from the groups consisting of NiTi alloy consisting essentially of 49–58 atom % Ni and the balance substantially Ti, CuZn alloy consisting essentially of 38.5–41.5 weight % Zn and the balance substantially Cu, CuZnX, consisting essentially of few weight % X, (X=Si, Sn, Al), NiAl alloy consisting essentially of 36–38 atom % Al and the balance substantially Ni, CuAlNi 14– 14.5 weight % Al, 3–4.5 weight % Ni, MnCu 5–35 atom % Cu, FeMnSi 32 weight % Mn, 6 weight % Si.

37. The guidewire of claim 23 wherein the tube has a plurality of orifices along the tube to cause progressively increasing flexibility towards the distal end of the tube.

38. The guidewire of claim 23 wherein the tube has the same length as the transition segment.

39. The guidewire of claim 23 wherein the tube has a length of about 10–40 cm.

40. The guidewire of claim 23 wherein the proximal end of the tube is adhesively bonded to the proximal end of the transition segment.

41. The guidewire of claim 23 wherein the transition segment has at least one radiopaque marker.

42. The guidewire of claim 23 having an outer surface with a lubricious coating applied thereto.

43. The guidewire of claim 23 wherein the tube has a wall thickness of between about 0.002 and 0.005 inches.

44. The guidewire of claim 23 wherein the elongate unitary core wire is formed of a stainless steel.

45. The guidewire of claim 23 wherein the elongate tube has a lower modulus than the transition segment.

* * * * *